United States Patent [19]

Akerfeldt

[11] Patent Number: 4,953,558

[45] Date of Patent: Sep. 4, 1990

[54] TISSUE SAMPLING DEVICE

[75] Inventor: Dan Akerfeldt, Uppsala, Sweden

[73] Assignee: C. R. Bard, Inc., Murray Hill, N.J.

[21] Appl. No.: 481,444

[22] Filed: Feb. 16, 1990

Related U.S. Application Data

[63] Continuation-in-part of Ser. No. 270,368, Nov. 14, 1988.

[30] Foreign Application Priority Data

Nov. 19, 1987 [SE] Sweden ............................ 8704559

[51] Int. Cl.⁵ ............................................ A61B 10/00
[52] U.S. Cl. ...................................... 128/751; 128/754; 606/171
[58] Field of Search ............... 128/305, 749, 751, 753, 128/754, 757; 604/21, 22, 51, 160, 164, 165, 166, 264; 606/167, 170, 171

[56] References Cited

U.S. PATENT DOCUMENTS

| 4,600,014 | 7/1986 | Beraha .............................. 128/754 |
| 4,699,154 | 10/1987 | Lindgren ............................ 128/754 |
| 4,776,346 | 10/1988 | Beraha et al. ..................... 128/754 |

*Primary Examiner*—Randall L. Green
*Assistant Examiner*—Randy Shay
*Attorney, Agent, or Firm*—Jones, Askew & Lunsford

[57] ABSTRACT

The present invention briefly refers to a driving unit for a device for tissue-sampling. The device comprises in addition to the driving unit a needle unit comprising a hollow outer needle and slidably disposed therein an inner needle, the driving unit being used to propel the needles. The driving unit comprises a driving device device for each mechanism adapted to be pre-tensioned. The driving unit in addition comprises an inner guide sleeve containing two successive needle holders adapted to be shifted in relation to each other in the longitudinal direction of the sleeve and adapted to be pretensioned in the same direction for propelling the needles with the aid of one spring each and which are provided with releasable locking means. A manual triggering device is provided for releasing the one needle holder which in turn is adapted during the final phase of its propulsion to release the other needle holder. A tensioning sleeve which rotatably surrounds the guide sleeve is provided with cam surfaces cooperating with the needle holders to pre-tension them against the spring force.

3 Claims, 5 Drawing Sheets

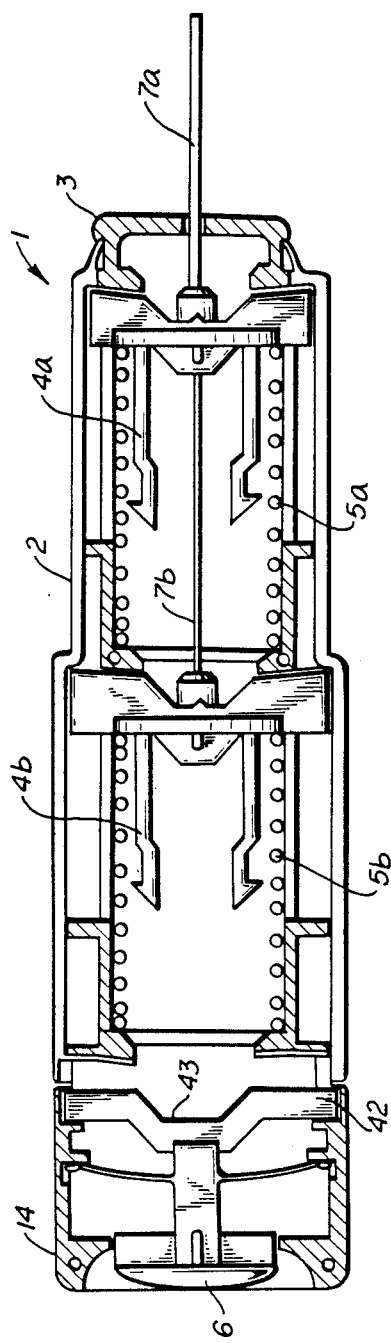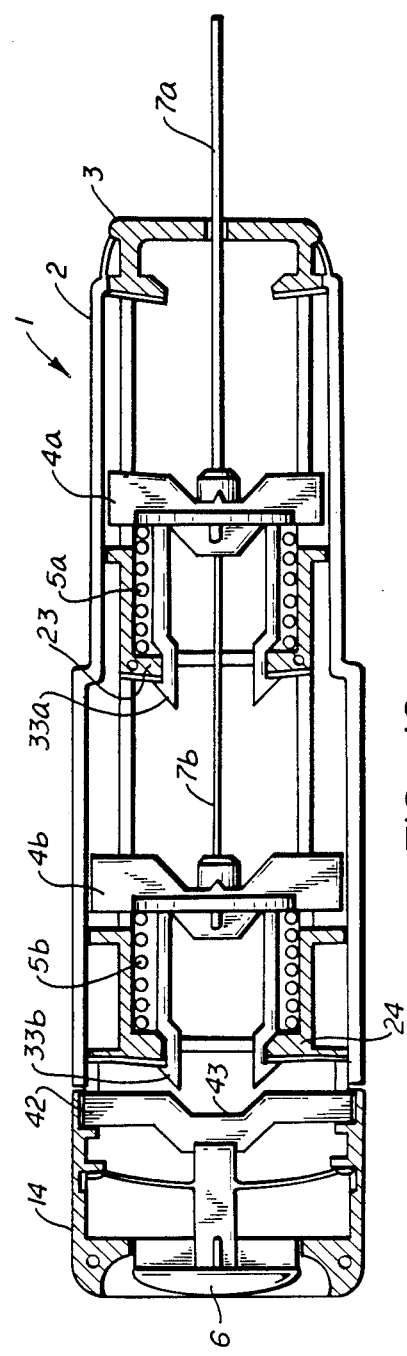
FIG. 9
FIG. 10

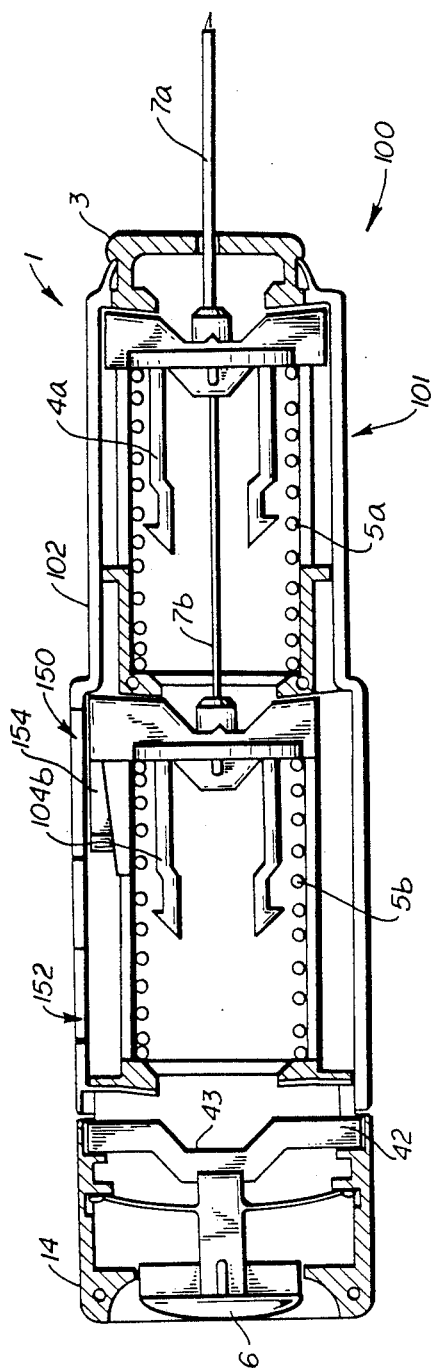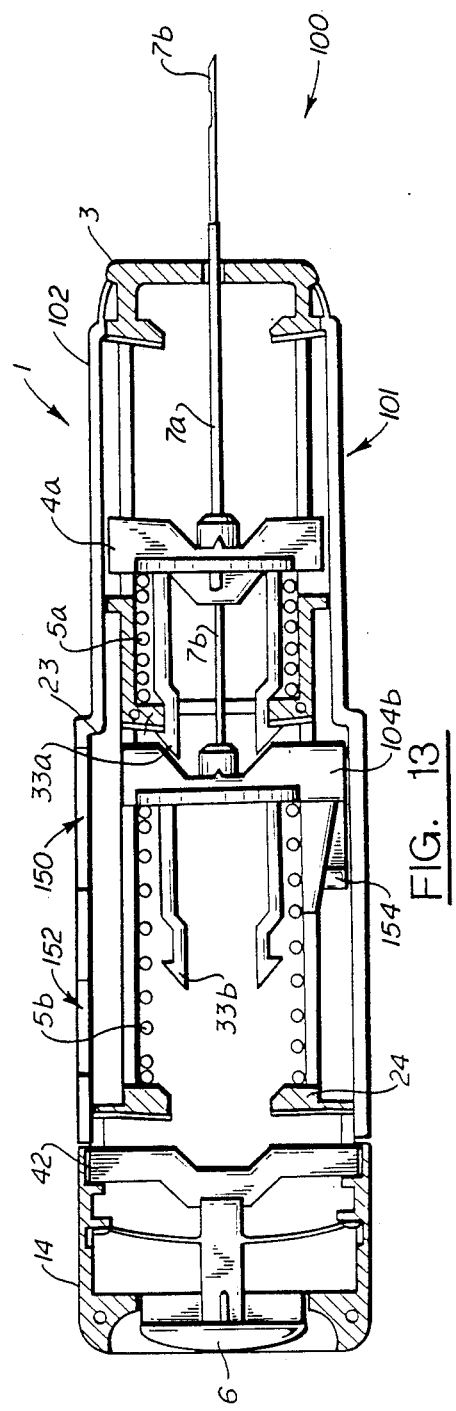
FIG. 12
FIG. 13

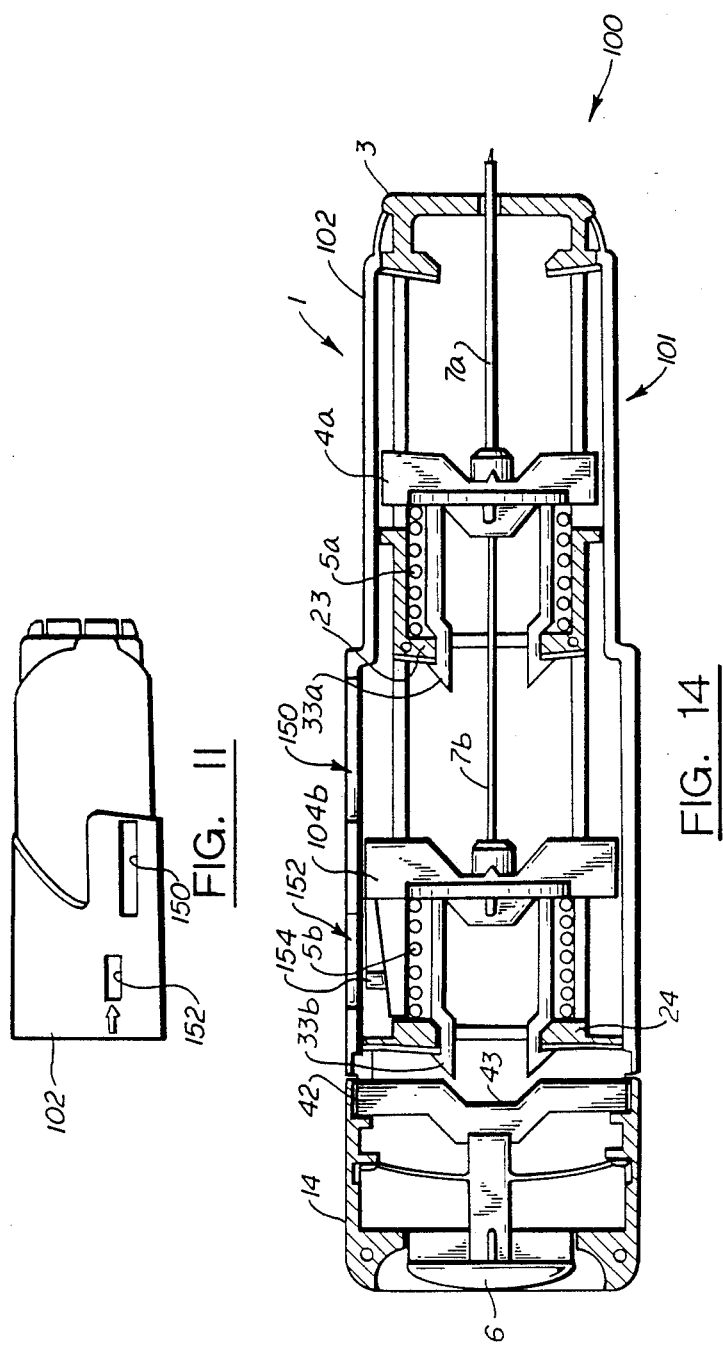

TISSUE SAMPLING DEVICE

Cross Reference to Related Application

This application is a continuation-in-part of my co-pending U.S. patent application Ser. No. 270,368, filed Nov. 14, 1988.

Technical Field

The present invention relates to devices for tissue sampling by so-called coarse-needle puncture in which a driving unit is used to drive the needle unit used for such a sampling. Specifically, the invention refers to a novel tissue sampling device wherein the needles are consecutively energized and wherein the driving unit provides a visual indication to the physician of whether the device is uncocked, half-cocked, or fully cocked.

Background of the Invention

In my co-pending U.S. patent application Ser. No. 270,368, of which the present application is a continuation-in-part, a tissue sampling device is described for retrieving a tissue specimen from a patient. The tissue sampling device comprises a hollow outer needle and a telescoping inner needle having a tissue sample receiving recess near its pointed forward end. A drive mechanism for driving the needles comprises springs for propelling the needles and latches for sequentially releasing the needles to be driven consecutively. In the disclosed embodiment, a tensioning sleeve mounted to the drive mechanism is rotated to sequentially energize the springs. When the device is actuated, the inner needle is first propelled forward by its corresponding spring; and when the inner needle has reached the forward extent of its travel, the hollow outer needle is released to be propelled forward by its corresponding spring.

The apparatus disclosed in my aforesaid U.S. patent application Ser. No. 270,368 provides a number of advantages over prior art tissue sampling devices. For example, in the device disclosed in U.S. Pat. No. 4,699,154, which discloses a similar type of sequentially spring-propelled device for obtaining a tissue specimen and which patent is incorporated herein by reference, both springs are energized simultaneously by pulling a handle. The device can require considerable effort to energize, since the physician must overcome the force of both springs at once. However, in the device disclosed in my co-pending U.S. patent application Ser. No. 270,368, the springs are energized sequentially, rather than simultaneously. Thus, the device is easier to cock, since the operator need overcome the force of only one spring at at time. Further, since it is possible to energize the device only partially, it is possible to retract the hollow outer needle without retracting the inner needle, thereby to expose the tissue sample receiving notch in the inner needle without removing the needle from the driving mechanism. Thus, this design makes practical a single-use tissue sampling apparatus.

However, this advantageous feature of being able to energize the needles consecutively presents a problem, in that it is not easily possible by looking at the exterior of the device to determine visually whether the device is uncocked, half-cocked, or fully cocked. Obviously, attempts to retrieve a tissue specimen with an uncocked or half-cocked instrument will be unsuccessful, and in fact the device disclosed in my aforesaid U.S. patent application Ser. No. 270,368 will not fire if the device is not fully cocked. But once the needle is inserted into a body cavity of a patient and it is thereafter determined by the physician that the instrument is uncocked or only partially cocked, the instrument cannot easily be further energized with the tip of the needle still within the body cavity of the patient without risk of injury to the patient. Rather, the instrument must be withdrawn, the tensioning sequence completed, and the needle tip then reintroduced into the body cavity. Such withdrawal and reintroduction increases the duration and discomfort of the procedure and increases the risk to the patient of injury or infection.

Thus, it would be desirable to provide a tissue sampling device of the type described which provides a visual indication to the physician indicating whether the instrument is fully energized, partially energized, or altogether uncocked.

Summary of the Invention

Stated generally, the present invention relates to a tissue sample retrieval device comprising a pair of telescoping spring-driven needles which are sequentially actuated, wherein the device is characterized by a means for providing a visual indication to the physician as to whether or not the instrument is fully energized.

Stated somewhat more specifically, the tissue sampling device of the present invention comprises a guide sleeve having front and rear guide sleeve ends and defining a longitudinal axis extending between the front and rear guide sleeve ends. A hollow first needle is positioned within the guide sleeve and extends from the front guide sleeve end. A second needle extends through the hollow first needle and has a tip which is extendable from the hollow first needle and a tissue sample receiving recess located adjacent the tip.

A first needle holder is coupled to the hollow first needle and is mounted within the guide sleeve for movement along the longitudinal axis of the guide sleeve so as to move the hollow first needle along the axis. Similarly, a second needle holder is coupled to the second needle and is also mounted within the guide sleeve for movement along the longitudinal axis of the guide sleeve to move the second needle along the axis. A first spring disposed within the guide sleeve and operatively associated with the second needle holder is capable of being placed into an energized mode to store energy. A first latch selectively releasable from outside the guide sleeve retains the first spring in the energized mode. Similarly, a second spring positioned within the guide sleeve and operatively associated with the first needle holder is capable of being placed into an energized mode to store energy. A second latch retains the second spring in the energized mode, and the second latch is releasable in response to and subsequent to release of the first spring.

A tensioning sleeve is rotatably mounted on the guide sleeve and is operative upon rotation thereof to move the first needle holder and the second needle holder along the axis towards the rear guide sleeve end to cause the first latch means to hold the first spring in the energized mode and to cause the second latch means to hold the second spring in the energized mode. An indicator means, operatively associated with one of the first and second needle holders and visible from without the tensioning sleeve, indicates the energized status of the first and second springs, whereby a user can visually confirm by viewing the indicator means whether the springs are in the energized modes.

When the first latch is released, the first spring propels the second needle holder along the axis towards the front guide sleeve end, such that the tip of the second needle is extended from the hollow first needle, whereby a tissue sample can be captured within the recess. In response to and subsequent to the release of the first spring, the second latch releases the second spring to propel the first needle holder along the axis towards the front guide sleeve end, the hollow first needle thereby being extended from the front guide sleeve end such that the recess of the second needle is enclosed by the hollow first needle.

Thus, it is an object of the present invention to provide an improved tissue sampling device for retrieving specimens of internal body tissue of a patient for biopsy.

It is another object of the present invention to provide a tissue sampling device of the type described which provides a visual indication to the physician indicating whether the instrument is fully energized, partially energized, or altogether de-energized.

Other objects, features, and advantages of the present invention will become apparent upon reading the following specification, when taken in conjunction with the drawings and the appended claims.

Brief Description of the Drawings

FIG. 9 is a section of the driving unit according to the invention in the released condition.

FIG. 10 is a section corresponding to FIG. 9 but showing the portions in their pre-tensioned condition.

FIG. 11 is a side view of a tensioning sleeve of an alternate embodiment of a tissue sample retrieving device according to the present invention.

FIG. 12 is a section of the driving unit of the alternate embodiment in a released condition.

FIG. 13 is a section of the driving unit of FIG. 12 showing the driving unit in a partially energized configuration.

FIG. 14 is a section of the driving unit of FIG. 12 showing the driving unit in a fully energized configuration.

Detailed Description of the Disclosed Embodiment

Figure 1:
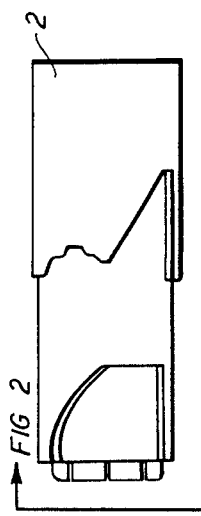
FIG. 1 is a side view of a sleeve forming the outer wall of the driving unit of a first embodiment of a tissue sampling device according to the present invention.
Figure 4:
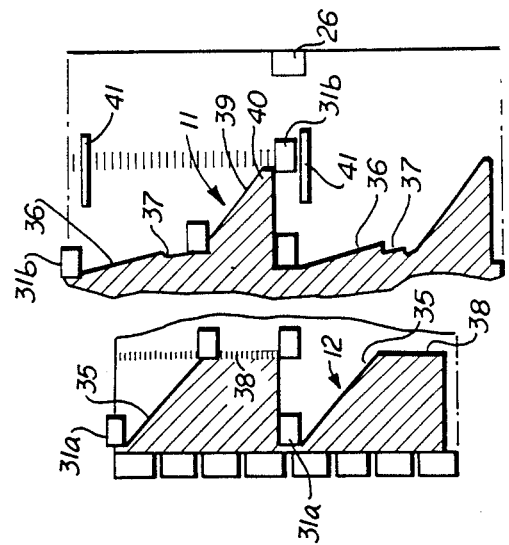
FIG. 4 is a flattened view of the sleeve shown in FIGS. 1-3.

Referring now to the drawings, in which like numerals indicate like elements throughout the several views, a first embodiment of a tissue sampling device for biopsy purposes is disclosed in FIGS. 1-10 and comprises a needle unit and a driving unit in combination. As mentioned initially, the needle unit and the sampling procedure are previously known and will therefore not be described in any great detail.

The driving unit 1 of the first embodiment comprises an outer tensioning sleeve 2 (FIGS. 1-4), an internal guide sleeve 3 (FIGS. 7 and 8), two needle holders 4a, 4b, two driving springs 5a, 5b, and a triggering knob 6 (FIGS. 9 and 10). Attached within the first or forward needle holder 4a is a tubular needle 7a whereas attached to the second or rear needle holder 4b is a solid needle 7b having a recess 8 (FIG. 5) for receiving a tissue sample, said latter solid needle 7b extending slidably through the tubular needle 7a.

Figure 2:
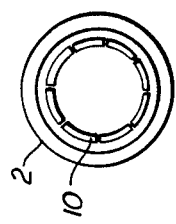
FIG. 2 is an end view of the sleeve shown in FIG. 1 seen in the direction of the arrows II—II.
Figure 3:
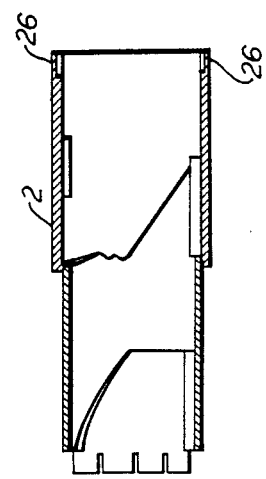
FIG. 3 is a central longitudinal section of the sleeve shown in FIGS. 1 and 2.

The outer sleeve or tensioning sleeve 2 forms the outer wall of the driving unit. At its narrow end the sleeve 2 carries a set of tongues 10, the free outer ends of which are radially pre-tensioned in an inward direction. The function of these tongues will become apparent as the assembly is explained hereinbelow. As seen in FIG. 2, the sleeve 2 is of substantially circular cross-section but has step-wise diminishing diameter. The steps between the various diameters form cam surfaces, a rear cam surface 11 and a forward cam surface 12, extending radially into the sleeve. In the embodiment shown these cam surfaces 11, 12 are double, which means that the cam surfaces 11, 12 are symmetrically repeated twice on the circumference. The shape and function of the cam surfaces 11, 12 will be described hereinbelow.

The inner sleeve or guide sleeve 3 comprises two identical halves 13 which may be put together in a conventional way with the aid of pins and holes to form a unit of substantially cylindrical shape and circular cross section. The guide sleeve 3 has a handle 14 formed at its rear end. At the forward end of the guide sleeve 3, an axially directed hole 15 is formed through which the needles 7a, 7b are to extend and which also serves as a guide for the needles. Also at the forward end a radially inwardly extending circular groove 16 is adapted to receive the tongues 10 of the tensioning sleeve 2. A circular depression 17 is provided on the handle 14 facing in an inward direction and adapted to be inserted into the tensioning sleeve 2 when the unit is assembled. The guide sleeve 3 also has two circular flanges 18, 19 adapted to abut against the inner surface of the tensioning sleeve 2. Two pairs of axially extending guide grooves 20, 21 in diametrically opposed positions extend through the wall of the guide sleeve 3.

Within the guide sleeve 3 a circular shoulder 22 is formed at the needle end and comprises an abutment for the forward needle holder 4a. Similarly, an intermediate circular shoulder 23 forms an abutment for the rear needle holder 4b and provides a seat for the driving spring 5a for the forward needle holder 4a. A rear circular shoulder 24 forms a seat for the driving spring 5b for the rear needle holder 4b. Both the rear shoulder 24 and the intermediate shoulder 23 also form parts of the locking mechanism during loading or tensioning of the driving unit of the sampling device, in particular if the driving springs 5a and 5b are compressed.

Within the handle 14 there are in addition provided two opposite axially extending grooves 25 cooperating with grooves or recesses 26 in the tensioning sleeve 2 to prevent the sampling device from being triggered except in one definite position, as well as guides for the triggering knob 6.

Figure 6:
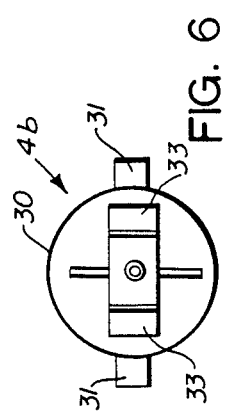
FIG. 6 is an end view of the end opposite to the needle of the needle holder shown in FIG. 5.
Figure 5:
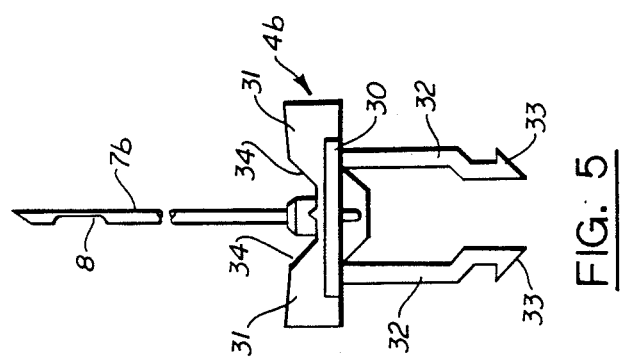
FIG. 5 is a side view of the needle holder of the solid needle of the first embodiment, it being understood that the needle holder for the tubular needle has a substantially corresponding shape.
Figure 7:
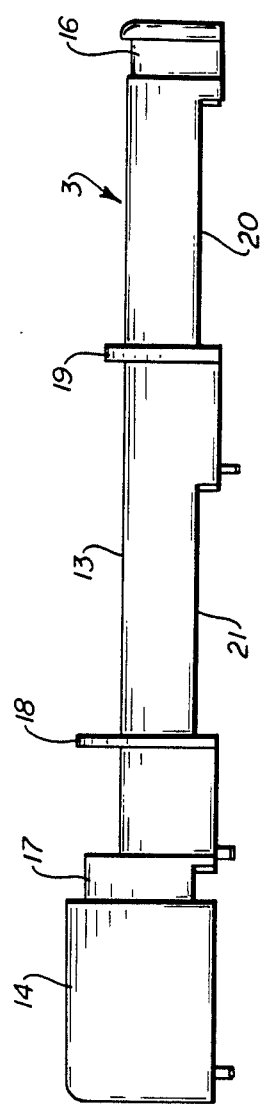
FIG. 7 is a side view of one half of the guide sleeve composed of two halves.
Figure 8:
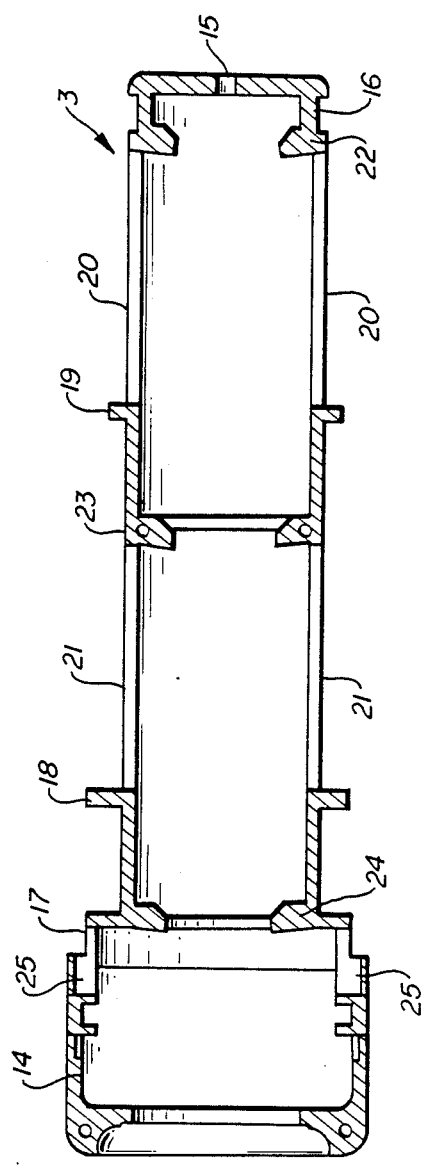
FIG. 8 is a plan view from the concave side of the sleeve half shown in FIG. 7.

As appears from FIGS. 5 and 6, each of the needle holders 4a, 4b comprises a body 30 having a width slightly narrower than the inner diameter of the guide sleeve 3. On the one side of the plate 30 a pair of radially extending wings 31 are provided extending slightly beyond the periphery of the plate 30. On the opposite side of the plate 30 a pair of axially extending arms 32 project rearward, said arms being resilient and provided at their outer free ends with outwardly extending hooks 33. These hooks 33 are adapted in the driving unit's tensioned condition to rest behind a shoulder 23 and 24 respectively, a pressure spring 5a, 5b being inserted about the arms 32 between the plate 30 and the respective shoulder 23, 24. Each of the wings 31 has a downward and inwardly sloping surface 34. For releasing the sampling device, these surfaces 34 cooperate with the hooks 33 of the arms 32, the hooks 33 sliding along the surfaces 34 and being shifted towards each other to release them from their engagement with the respective shoulder 23, 24.

The wings 31 are guided in slots 20, 21 thus preventing rotation of the needle holders 4a, 4b in relation to the guide sleeve 3. The wings 31 extend through the axially extending guide slots 20, 21 in the guide sleeve 3 and towards the inner surface of the tensioning sleeve 2 to engage the cam surfaces 11, 12 formed thereon.

The assemblage of the driving unit 1 is performed substantially in the manner now to be described. The two needle holders 4a, 4b together with their needles 7a, 7b and with the springs 5a, 5b positioned about their arms 32 are placed in position in the one half of the guide sleeve 3. The trigger knob 6 is also inserted in the one half of the guide sleeve, whereafter the other half of the guide sleeve 3 is assembled onto the first half with the pins in one guide sleeve half engaging corresponding holes in the other guide sleeve half. Thereafter, the tensioning sleeve 2 is passed axially over the guide sleeve 3, causing the tongues 10 to engage the groove 16, while the opposite end of the tensioning sleeve 2 encloses the guide sleeve 3 at the depression 17. In this position the unit is ready for use. It will be appreciated that the parts used are of simple and cheap construction, to the extent possible consisting of plastics or similar materials, only springs 5a, 5b and the needles 7a, 7b proper consisting of metal and in addition being lightweight.

The driving unit of the sampling device operates in the manner now to be described. The sampling device, which in itself is of the single-use type, may be loaded several times without problems and is manufactured with different needle thicknesses and needle lengths depending on the intended use. The physician thus chooses a sampling device adapted for the sampling in question. This device, however, is not initially tensioned in order to avoid deformation of certain parts due to the spring forces, but tensioning is to be performed immediately prior to sampling. For this purpose the handle 14 is held with the one hand while the other hand seizes the tensioning sleeve 2 to perform relative rotation of these parts. As the handle is rotated relative to the sleeve, the wings 31a of the forward needle holder 4a are shifted along the steep portion of the cam surface 12, thereby compressing the forward spring 5a. The wings 31b of the rear needle holder 4b follow at the same time the flattened portion 36 of the cam surface 11 to arrive at the end behind catch 37. In this position backward rotation to the starting position is no longer possible, but the rear needle holder 4b is raised to such an extent that it cannot come into contact with the hooks 33a of the forward needle holder 4a when these enter into the locking position behind the intermediate shoulder 23. During continued rotation the forward wings 31a follow the plane cam surface 38a whereas the rear wings 31b follow the steep cam surface 39 causing the rear spring 5b to be compressed. If the physician should lose his grip during this part of the tensioning procedure, the rear needle holder 4b moves towards the starting position but is retained in front of catch 37 and thus cannot release the forward needle holder 4a.

When the wings 31b have been advanced along cam surface 39 during continued rotation, they are lifted over a catch 40. Thereafter reverse rotation is impossible and continued rotation is prevented by an abutment 41. In this position the recesses 26 are situated exactly opposite grooves 25 in the guide sleeve 3 and the triggering knob 6 may be depressed. The sampling device is now tensioned and ready for sampling.

The triggering knob 6 is connected to a cross element 42 having a substantially V-shaped depression 43 in its central portion. When the triggering knob 6 is depressed, which is possible due to the fact that grooves 25 and 26 are mutually aligned, the flanges of the V-shaped portion 43 will bias the hooks 33b towards each other, causing them to lose contact with the shoulder 24 and enabling the spring 5b to propel the inner needle 7b forward. When the rear needle holder 4b approaches the shoulder 23 at the forward extent of its travel, the sloping surfaces 34 on the forward portion of the rear needle holder 4b engage the hooks 33a on the forward needle holder 4a, biasing the hooks inwardly and disengaging them from the shoulder 23. The forward needle holder 4a is thereby released from its engagement with the intermediate shoulder 23 to be propelled forward by its corresponding spring 5a. Consequently, the solid inner needle 7b, with its tissue-receiving cavity 8 formed adjacent its tip, is propelled first, whereafter the tubular outer needle 7a is released to resect the tissue received in said cavity. If additional samples are to be taken, the tubular needle 7a is retracted to provide access to the recess 8 and the tissue sample captured therewithin, which is accomplished by rotating the sleeve 2 in relation to the handle 14 to the first locking position in which the wings 31b are retained behind the catch 37.

The sequential tensioning sequence hereinabove described, wherein rotation of the tensioning sleeve energizes first one spring and then the other, provides the advantage that, since only one spring at a time is being energized, the physician need exert only enough force on the tensioning sleeve to overcome the force of one spring, rather than having to overcome the force of both springs simultaneously. However, this sequential cocking arrangement presents the possibility that the physician might unknowingly energize only the first spring and go no further, not realizing that the driving device is not fully energized. To overcome this problem, an alternate embodiment of a tissue sampling device 100 according to the present invention, disclosed in FIGS. 11-14, comprises a means for providing a visual indication to the physician that the device is fully energized, only partially energized, or completely uncocked.

The alternate embodiment of the tissue sampling device 100 includes a driving unit 101 which is in many respects identical to the driving unit 1 of the previously described embodiment. Therefore, for purposes of the description of the alternate embodiment of the tissue sampling device 100, only those elements which differ from their corresponding elements of the driving unit 1 will now be described, it being understood that the remaining elements are identical to the corresponding elements of the driving unit 1.

The driving unit 101 of the alternate embodiment 100 includes a tensioning sleeve 102 which differs from the tensioning sleeve 2 previously described only in that the tensioning sleeve 102 includes a pair of windows formed therethrough. The exact location and purpose of these windows 150, 152 will be more fully described below.

The driving unit 101 comprises a pair of needle holders 4a and 104b. The first or forward needle holder 4a has the tubular needle or cannula 7a attached thereto, and the second or rear needle holder 104b has the solid needle or stylet 7b attached thereto. The rear needle holder 104b differs from the rear needle holder 4b of the previously disclosed embodiment in that the rear needle holder 104b includes an indicator element 154 extending rearward from one of the radially extending wings 31. In the disclosed embodiment, the indicator element 154 is molded from a plastic having a contrasting color to the sleeve 102 for ready visibility and has an arrow inscribed thereon. When the rear needle holder 104b is installed in the guide sleeve 3 in the manner depicted in FIGS. 12-14, the indicator element 154 is disposed in the annular space between the guide sleeve 3 and the tensioning sleeve 102 and extends rearward in a direction substantially parallel to the inner wall of the tensioning sleeve.

The locations of the windows 150, 152 in the tensioning sleeve 102 are determined with respect to the forwardmost and rearwardmost positions of the indicator element 154 on the rear needle holder 104b, as will be explained with reference to FIGS. 12-14. The forward window 150 is disposed such that when the driving unit 101 is in its released or untensioned condition with the rear needle holder 104b in its forwardmost position, as illustrated in FIG. 12, the indicator element 154 on the rear needle holder is aligned with the window 150 so as to be visible therethrough. Similarly, the rear window 152 is located such that when the driving unit 101 is in its fully tensioned state with the rear needle holder 104b in its rearmost position, as depicted in FIG. 14, the indicator element 154 on the rear needle holder corresponds with the location of the rear window 152 so as to be visible therethrough.

Assembly of the driving unit 101 of the alternate embodiment 100 is essentially the same as the assembly of the driving unit 1 of the previously disclosed embodiment. The rear needle holder 104b is assembled onto the guide sleeve 3 with the radial wings 31 of the rear needle holder riding in the longitudinal slots 21 of the guide sleeve and the indicator element 154 disposed outwardly of the guide sleeve. Also, when assembling the tensioning sleeve 102 onto the guide sleeve 3, care must be taken to align the tensioning sleeve rotationally so that the indicator element 154 is visible through the front window 150 when the driving unit is in its untensioned configuration.

Operation of the alternate embodiment of the tissue sampling device 100 will now be described. The driving unit 101 of the tissue sampling device 100 is energized in the same manner as hereinabove described with respect to the driving unit 1 of the previously described embodiment. In the untensioned condition, as shown in FIG. 12, the forward needle holder 4a and the rear needle holder 104b are both in their forwardmost positions, and the indicator element 154 is visible through the front window 150, indicating to the physician that the unit is uncocked. To initiate the energizing sequence, the physician holds the tensioning sleeve stationary in one hand while rotating the handle 14 of the device with the other. As the handle 14 is rotated through the first 180° of movement, the forward cam surface on the inner wall of the tensioning sleeve 102 biases the front needle holder 4a rearward in the same manner hereinabove described with respect to the drive unit 1 of the previously disclosed embodiment. In this partially cocked configuration, illustrated in FIG. 13, the front needle head 4a is in its rearmost position, while the rear needle holder 104b is still in its forwardmost position. Also in this configuration, the rear needle holder 104b has been rotated 180° from its beginning position such that the indicator element 154 is on the side of the driving unit opposite the window 150 in the tensioning sleeve. Thus, even though the rear needle holder 104b has not moved axially from its initial position, the indicator element 154 is nonetheless not visible through either of the windows 150, 152.

As the energizing sequence is continued, the handle 14 is rotated an additional 180° with respect to the tensioning sleeve 102 until the drive unit 101 attains the fully energized state illustrated in FIG. 14. In this fully tensioned state, both needle holders 4a, 104b are in their rearmost positions. The rear needle holder has now been rotated a full 360° from its initial position such that the indicator element 154 is once again on the same side of the drive unit as the windows 150, 152. However, the rear needle holder 104b has now been biased to its rearmost position such that the indicator element is visible through the rear window 152, rather than the front window 150.

The physician may thus visually confirm the cocking status of the driving unit 101 by observing the windows 150, 152 in the tensioning sleeve 102. If the indicator element 154 on the second needle holder 104b can be seen through the front window 150 in the tensioning sleeve 102, the physician knows that the driving unit 101 is fully uncocked. If the indicator element 154 is not visible through either of the two windows 150, 152, then the physician will know that the driving unit 101 is partially cocked, that is, the front needle holder 4a is cocked but the rear needle holder 104b is still uncocked. If the indicator element 154 is visible through the rear window 42 in the tensioning sleeve 2, then the physician knows that the driving unit 1 is fully energized and ready for use. This feature of windows in the tensioning sleeve through which an indicator element can be viewed to provide a visual indication to the physician whether the instrument is fully energized, partially energized, or altogether uncocked is particularly advantageous in the sequentially energized embodiment, so that the physician will not attempt to use an uncocked or only partially cocked device.

While the alternate embodiment 100 of the tissue sampling device has been disclosed with respect to a tensioning sleeve 102 having windows 150, 152 located to correspond to an indicator element 154 on the rear needle holder, it will be appreciated that similar results can be obtained by locating the indicator element on the front needle holder and moving the windows forward correspondingly. In such an arrangement, a front window would be disposed to reveal the indicator element when the driving unit is in its fully uncocked or released condition, while the rear window would be located so as to reveal the indicator element when the driving unit is in its fully tensioned or fully energized state. When the driving unit has been only partially energized, the front needle holder will have been moved to its rearmost position but will also have been rotated 180° so as not to be visible through either of the windows. When the driving unit has been fully cocked, the front needle holder will have been rotated a full 360° and will now be visible through the rear window.

In addition, while the driving unit 101 has been disclosed with respect to an embodiment having a pair of windows 150, 152, it will be appreciated that satisfactory, though somewhat less informative, results may be achieved by a tensioning sleeve having only a single window aligned to reveal an indicator element only when the driving unit has been completely cocked. While such an arrangement would indicate only whether or not the device is fully energized and would not differentiate between a driving unit which is completely released and a driving unit which is partially energized, this arrangement would nonetheless indicate to the physician that further energizing is necessary before the unit is ready for use and hence would provide a significant advantage over the drive unit 1 of the previously disclosed embodiment which does not have any means whatsoever of providing a visual confirmation that the device is cocked.

Finally, it will be understood that the foregoing embodiments have been disclosed by way of example, and that other modifications may occur to those skilled in the art without departing from the scope and spirit of the appended claims.

What is claimed is:

1. A tissue sampling device comprising:
   a guide sleeve having front and rear guide sleeve ends and defining a longitudinal axis extending between said front and rear guide sleeve ends;
   a hollow first needle positioned within said guide sleeve and extendable from said front guide sleeve end, said hollow first needle being moveable along said axis;
   a second needle extending through said hollow first needle and movable along said axis, said second needle having a tip which is extendable from said hollow first needle and said front guide sleeve end, and said second needle having a tissue sample receiving recess located adjacent said tip;
   a first needle holder coupled to said hollow first needle and mounted within said guide sleeve for movement along said longitudinal axis to move said hollow first needle along said axis;
   a second needle holder coupled to said second needle and mounted within said guide sleeve for movement along said longitudinal axis to move said second needle along said axis;
   a first spring disposed within said guide sleeve and operatively associated with said second needle holder, said first spring being capable of being placed into an energized mode to store energy, and said first spring being releasable from said energized mode to propel said second needle holder along said axis towards said front guide sleeve end, such that said tip of said second needle is extended from said hollow first needle, whereby a tissue sample can be captured within said recess;
   a second spring positioned within said guide sleeve and operatively associated with said first needle holder, said second spring being capable of being placed into an energized mode to store energy, and said second spring being releasable from said energized mode to propel said first needle holder along said axis towards said front guide sleeve end, said hollow first needle being extended from said front guide sleeve end such that said recess of said second needle is enclosed by said hollow first needle;
   a first latch means selectively releasable from outside said guide sleeve for releasably holding said first spring in said energized mode;
   a second latch means for releasably holding said second spring in said energized mode, said second latch means being releasable in response to and subsequent to release of said first spring;
   a tensioning sleeve rotatably mounted on said guide sleeve and operative upon rotation thereof to move said first needle holder and second needle holder along said axis towards said rear guide sleeve end to cause said first latch means to hold said first spring in said energized mode and to cause said second latch means to hold said second spring in said energized mode; and
   indicator means operatively associated with one of said first and second needle holders and visible from without said tensioning sleeve for indicating the energized status of said first and second springs;
   whereby a user can visually confirm by viewing said indicator means whether said springs are in said energized modes.

2. The tissue sampling device of claim 1, wherein said indicator means operatively associated with one of said first and second needle holders comprises an indicator formed on one of said first and second needle holders and extending outside said guide sleeve, and wherein said tissue sampling device further comprises means defining a window in said tensioning sleeve, said window being positioned such that said indicator formed on one of said first and second needle holders is visible through said window only when said first and second springs are both energized.

3. The tissue sampling device of claim 2, wherein said means defining a window in said tensioning sleeve comprises means defining a first window, and wherein said tissue sampling device further comprises means defining a second window in said tensioning sleeve, said second window being positioned such that said indicator formed on said one of said first and second needle holders is visible through said second window only when neither of said first and second springs is energized.

* * * * *